(12) United States Patent
Chen et al.

(10) Patent No.: US 6,955,880 B2
(45) Date of Patent: Oct. 18, 2005

(54) **PRIMER COMPOSITION AND METHOD OF USING THE SAME IN THE DETECTION OF *SHIGELLA SONNEI***

(75) Inventors: Jiann-Hwa Chen, Taichung (TW); Wen-Bin Hsu, Taichung (TW); Pei-Chun Chen, Taichung (TW)

(73) Assignee: National Chung Hsing University, Taichung City (TW)

( * ) Notice: Subject to any disclaimer, the term of this patent is extended or adjusted under 35 U.S.C. 154(b) by 537 days.

(21) Appl. No.: 10/200,927

(22) Filed: Jul. 23, 2002

(65) Prior Publication Data

US 2004/0038211 A1 Feb. 26, 2004

(51) Int. Cl.$^7$ .............................................. C12Q 1/68
(52) U.S. Cl. ....................................................... 435/6
(58) Field of Search ................. 435/6, 91.2; 536/24.33, 536/24.3

(56) References Cited

U.S. PATENT DOCUMENTS 5,958,686 A    9/1999   Houng

OTHER PUBLICATIONS

Houng, H.H. et al. "A Simple Polymerase Chain Reaction Technique To Detect And Differentiate Shigella And Enteroinvasive Escherichia Coli in Human Feces." Diagn Microbiol Infect Dis. (1997) 28 pp 19–25.

*Primary Examiner*—Jeffrey Fredman
*Assistant Examiner*—Heather G. Calamita
(74) *Attorney, Agent, or Firm*—Ladas & Parry LLP (57) ABSTRACT

The invention provides a new primer composition for detecting the presence of *Shigella sonnei* and a method of using the same. The primer composition and method have high specificity and sensitivity on the detection of *Shigella sonnei*.

5 Claims, 10 Drawing Sheets

SEQUENCE LISTING

<160> NUMBER OF SEQ ID NOS: 2

<210> SEQ ID NO 1
<211> LENGTH: 16
<212> TYPE: DNA
<213> ORGANISM: Artificial
<220> FEATURE:
<223> OTHER INFORMATION: Primer for amplifying DNA of Shigella sonnei

<400> SEQUENCE: 1
atgccgggca actgca                                              16

<210> SEQ ID NO 2

```
<211> LENGTH: 16
<212> TYPE: DNA
<213> ORGANISM: Artificial
<220> FEATURE:
<223> OTHER INFORMATION: Primer for amplifying DNA of Shigella sonnei

<400> SEQUENCE: 2
ctgcgtatst cgcttg                                                                16
```

PRIMER COMPOSITION AND METHOD OF USING THE SAME IN THE DETECTION OF *SHIGELLA SONNEI*

BACKGROUND OF THE INVENTION

1. Field of the Invention

The present invention relates to a new primer composition and a method of using the primer composition in the detection of *Shigella sonnei*.

2. Description of the Prior Art

Organisms of the genus *Shigella* cause classic bacillary dysentery that is characterized by severe diarrhea, fever and abdominal pain. *Shigella* is one of *Enterobacteriacea* and can be classified into four species: *S. dysenteriae*, *S. flexneri*, *S. boydii* and *S. sonnei*. *Shigella* spp. is typically associated with self-limiting infections that are rarely fatal except in children or the elderly. Infection with *S. dysenteriae* can cause a severe form of the disease with up to 20% of cases proving fatal, such as hemorrhagic colitis and hemolytic uremic syndrome. Although the syndromes caused by the infection with *S. flexneri*, *S. boydii* and *S. sonnei* are not so severe and can be cured by antibiotics, the general use of antibiotics results in the production of strains resistant against antibiotics. Moreover, *S. sonnei* infection frequently occurs in the industrially developed area. The *S. sonnei* infection will be popular in the industrial area of a high population density. Normally, the human by intake of 10–100 bacteria cells will be infected (DuPont et al., 1989, J. infect. Dis.).

Morris et al. indicated that the isolation percent of *Shigella* spp. samples was lower than 25%. That is, more than 75% of samples existing *Shigella* spp. could not be correctly detected (Morris et al., 1970, Appl. Microbiol.). Polymerase chain reaction (PCR) can be rapid and reliable for detecting bacteria and virus in various samples. It was described in Josephson et al., 1993, App. Environ. Microbiol that the PCR can detect the *S. sonnei* that cannot be cultivated. However, the method cannot specifically detect the existence of *S. sonnei*. Accordingly, there is a need to provide a method for a rapid and specific detection of *S. sonnie* in food and clinical samples.

SUMMARY OF THE INVENTION

One object of the invention is to provide a primer composition that amplifies a 369 base pair DNA of *Shigella sonnei*, said composition comprising the primers IS1SS and IS1SR3 wherein the primer IS1SS comprises the sequence as defined in SEQ ID NO:1 and the primer IS1SR3 comprises the sequence as defined in SEQ ID NO:2.

Another object of the invention is to provide a method for detecting *Shigella sonnei* in a solution sample, which comprises the following steps:

(a) incubating said sample with primers IS1SS and IS1SR3 in a PCR reaction solution whereby a PCR reaction takes place and amplifies nucleic acids to produce a 369 base pair amplification product;

(b) detecting the presence of a 369 base pair amplification product;

(c) splicing the 369 base pair amplification product by restriction enzyme BstEII;

(d) detecting the presence of the DNA fragments of the 88 base pair and 281 base pair; wherein the presence of said DNA fragments are indicative of the presence of *Shigella sonnie* in the sample.

BRIEF DESCRIPTION OF THE DRAWINGS

FIG. 2 shows the electrophoresis plot of the samples of *Escherichia coli* W3110 (ATCC 27325), *Sallmonella choleraesuis* (ATCC 13311), *Klebsiella pneumoniae* (ATCC 13883), *Serratia marcescens* (ATCC 13880), *Enterobacter aerogenes* (ATCC 13048) and *Enterobacter cloacae* (ATCC 13047); Lane 1: 100 bp marker; Lane 2: *Klebsiella pneumoniae* diluted by $10^2$ times; Lane 3: *Klebsiella pneumoniae* diluted by $10^3$ times; Lane 4: *Sallmonella choleraesuis* diluted by $10^2$ times; Lane 5: *Sallmonella choleraesuis* diluted by $10^3$ times; Lane 6: *Serratia marcescens* diluted by $10^2$ times; Lane 7: *Serratia marcescens* diluted by $10^3$ times; Lane 8: *Enterobacter cloacae* diluted by $10^2$ times; Lane 9: *Enterobacter cloacae* diluted by $10^3$ times; Lane 10: *Enterobacter aerogenes* diluted by $10^2$ times; Lane 11: *Enterobacter aerogenes* diluted by $10^3$ times; Lane 12: *Escherichia coli* W3110 diluted by $10^2$ times; Lane 13: *Escherichia coli* W3110 diluted by $10^3$ times; Lane 14: *S. flexneri* diluted by 102 times; lane 15: sterile water; Lane 16: 100 bp marker.

FIG. 5 shows the electrophoresis plot of the samples isolated from ground water and incubated at 25° C.; (A) Lane 1: 100 bp marker; Lane 2: *O. ureolytica/urethralis* diluted by $10^2$ times; Lane 3: *O. ureolytica/urethralis* diluted by $10^3$ times; Lane 4: *X. maltophilia* diluted by $10^2$ times; Lane 5: *X. maltophilia* diluted by $10^3$ times; Lane 6: the strain diluted by $10^2$ times that could not be identified; Lane 7: the strain diluted by $10^3$ times that could not be identified; Lane 8: sterile water; Lane 9: *S. sonnei* diluted by $10^2$ times; Lane 10: 100 bp marker; (B) Lane 1: 100 bp marker; Lane 2: *A. delafieldii* diluted by $10^2$ times; Lane 3: *A. delafieldii* diluted by $10^3$ times; Lane 4: the strain-1 diluted by $10^2$ times that was not identified; Lane 5: the strain-1 diluted by $10^3$ times that was not identified; Lane 6: *X. maltophilia* diluted by $10^2$ times; Lane 7: *X. maltophilia* diluted by $10^3$ times; Lane 8: *A. genospecies* 15 diluted by $10^2$ times; Lane 9: *A. genospecies* 15 diluted by $10^3$ times; Lane 10: the strain-2 diluted by $10^2$ times that was not identified; Lane 11: the strain-2 diluted by $10^3$ times that was not identified; Lane 12: *S. sonnei*; Lane 13: sterile water; Lane 14: 100 bp marker.

FIG. 7 shows the BstEII sliced fragments of the 369 bp PCR products of *S. boydii* (ATCC 8700), *S. dysenteriae* (ATCC 4837), *S. flexneri* (ATCC 29903), *S. sonnei* (ATCC 29930), *E. Coli* W3110 (ATCC 27325), *E. aerogenes* (ATCC 13048), *S. odorifera, P. agglomerans* and *S. marcescens;* the lanes of odd numbers represent the PCR products that were not cut by the BstEII and the lanes of even numbers represent the PCR products that were cut by the BstEII; (A) Lane M: 100 bp marker; Lanes 1 and 2: *S. sonnei* (ATCC 19930); Lanes 3 and 4: *S. flexneri* (ATCC 29903); Lanes 5 and 6: *S. boydii* (ATCC 8700); Lanes 7 and 8: *S. dysenteriae* (ATCC 4837); Lanes 9 and 10: *E. aerogenes* (ATCC 13048); Lanes 11 and 12: *E. coli* W3110 (ATCC 27325); Lanes 13 and 14: *S. odorifera*; (B) Lanes 1 and 2: *Acinetobacter calcoacet/baumannii*/gen 2; Lanes 3 and 4: *S. marcescens*.

FIG. 8 shows the electrophoresis plot of the samples of *S. sonnei* ATCC 9290, ATCC 11060, ATCC 25931, ATCC 20920 and ATCC 29031; (a) Lane 1: 100 bp marker; Lane 2: *S. sonnei* ATCC 9290 diluted by $10^7$ times; Lane 3: *S. sonnei* ATCC 9290 diluted by $10^8$ times; Lane 4: *S. sonnei* ATCC 9290 diluted by $10^9$ times; Lane 5: *S. sonnei* ATCC 9290 diluted by $10^{10}$ times; Lane 6: *S. sonnei* ATCC 9290 diluted by $10^{11}$ times; Lane 7: *S. sonnei* ATCC 11060 diluted by $10^7$ times; Lane 8: *S. sonnei* ATCC 11060 diluted by $10^8$ times; Lane 9: *S. sonnei* ATCC 11060 diluted by $10^9$ times; Lane 10: *S. sonnei* ATCC 11060 diluted by $10^{10}$ times; Lane 11: *S. sonnei* ATCC 11060 diluted by $10^{10}$ times; Lane 12: sterile water; Lane 13: *S. sonnei*; Lane 14: 100 bp marker; (b) Lane 1: 100 bp marker; Lane 2: *S. sonnei* ATCC 25931 diluted by $10^8$ times; Lane 3: *S. sonnei* ATCC 25931 diluted by $10^9$ times; Lane 4: *S. sonnei* ATCC 25931 diluted by $10^{10}$ times; Lane 5: *S. sonnei* ATCC 20920 diluted by $10^6$ times; Lane 6: *S. sonnei* ATCC 20920 diluted by $10^7$ times; Lane 7: *S. sonnei* ATCC 20920 diluted by $10^8$ times; Lane 8: *S. sonnei* ATCC 20920 diluted by $10^9$ times; Lane 9: *S. sonnei* ATCC 20920 diluted by $10^{10}$ times; Lane 10: sterile water; Lane 11: *S. sonnei* ATCC 29031 diluted by $10^8$ times; Lane 12: *S. sonnei* ATCC 29031 diluted by $10^9$ times; Lane 13: *S. sonnei* ATCC 29031 diluted by $10^{10}$ times; Lane 14: sterile water; Lane 15: *S. sonnei*; Lane 16: 100 bp marker.

FIG. 9 shows the electrophoresis plots of the samples of *S. Sonnei* SH 7105, SH 8255, SH 9397, SH 8069, SH 10567, South 27 and South 36 diluted by serial 10 times; (a) Lane 1: 100 bp marker; Lane 2: *S. sonnei* (ATCC 29930) diluted by $10^6$ times; Lane 3: *S. sonnei* (SH 7105) diluted by $10^8$ times; Lane 4: *S. sonnei* (SH 7105) diluted by $10^9$ times; Lane 5: *S. Sonnei* (SH 7105) diluted by $10^{10}$ times; Lane 6: *S. Sonnei* (SH 8255) diluted by $10^8$ times; Lane 7: *S. sonnei* (SH 8255) diluted by $10^9$ times; Lane 8: *S. sonnei* (SH 8255) diluted by $10^{10}$ times; Lane 9: sterile water; Lane 10: *S. sonnei* (SH 9397) diluted by $10^8$ times; Lane 11: *S. sonnei* (SH 9397) diluted by $10^9$ times; Lane 12: *S. sonnei* (SH 9397) diluted by $10^{10}$ times; Lane 13: *S. sonnei* (SH 8069) diluted by $10^8$ times; Lane 14: *S. sonnei* (SH 8069) diluted by $10^9$ times; Lane 15: *S. sonnei* (SH 8069) diluted by $10^{10}$ times; Lane 16: sterile water; Lane 17: 100 bp marker; (b) Lane 1: 100 bp marker; Lane 2: *S. sonnei* (SH 10567) diluted by $10^7$ times; Lane 3: *S. sonnei* (SH 10567) diluted by $10^8$ times; Lane 4: *S. sonnei* (SH 10567) diluted by $10^9$ times; Lane 5: *S. sonnei* (SH 10567) diluted by $10^{10}$ times; Lane 6: *S. sonnei* (SH 10567) diluted by $10^{11}$ times; Lane 7: *S. sonnei* (SH 10567) diluted by $10^{12}$ times; Lane 8: sterile water; Lane 9: *S. sonnei* (ATCC 29930) diluted by $10^6$ times; Lane 10: 100 bp marker; (c) Lane 1: 100 bp marker; Lane 2: *S. sonnei* (south 27) diluted by $10^6$ times; Lane 3: *S sonnei* (south 27) diluted by $10^7$ times; Lane 4: *S. sonnei* (south 27) diluted by $10^8$ times; Lane 5: *S. sonnei* (south 27) diluted by $10^9$ times; Lane 6: *S. sonnei* (south 27) diluted by $10^{10}$ times; Lane 7: *S. sonnei* (south 27) diluted by $10^{11}$ times; Lane 8: sterile water; Lane 9: *S. sonnei* (ATCC 29930) diluted by $10^6$ times; Lane 10: 100 bp marker; (d) Lane 1: 100 bp marker; Lane 2: *S. sonnei* (south 36) diluted by $10^9$ times; Lane 3: *S. sonnei* (south 36) diluted by $10^{10}$ times; Lane 4: *S. sonnei* (south 36) diluted by $10^{11}$ times; Lane 5: sterile water; Lane 6: *S. sonnei* (ATCC 29930) diluted by $10^6$ times; Lane 7: 100 bp marker.

DETAILED DESCRIPTION OF THE INVENTION

The invention provides a new primer composition for detecting the presence of *Shigella sonnei* and a kit and method of using the same.

One object of the invention is to provide a primer composition that amplifies a 369 base pair DNA of *Shigella sonnei*, said composition comprising the primers IS1SS and IS1SR3 wherein the primer IS1SS comprises the sequence as defined in SEQ ID NO:1 and the primer IS1SR3 comprises the sequence as defined in SEQ ID NO:2.

According to the invention, the term "primer" as used herein refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, i.e. in the presence of nucleotides and an inducing agent such as DNA polymerase and at a suitable temperature and pH. The primer composition of the invention comprises the primers IS1SS and IS1SR3. The sequences of the primers IS1SS and IS1SR3 are as follows:

IS1SS:    5'-ATGCCGGGCAACTGCA-3'    (SEQ ID NO: 1)

IS1SR3:   5'-CTGCGTATSTCGCTTG-3'    (SEQ ID NO: 2)

According to the invention, the primers IS1SS and IS1SR3 typically comprise 16 nucleotides, respectively. The IS1SS and IS1SR3 amplify a 369 base pair DNA of *Shigella sonnei*. A length of the primers IS1SS and IS1SR3 is variable as long as they maintain their original function. As nucleic acids do not require complete complementarity in order to hybridize, it is to be understood that the primer sequences herein disclosed may be modified to some extent without loss of utility as the 369 base pair DNA-specific primers. As is known in the art, a hybridization of complementary or partially complementary nucleic acid sequences may be obtained by adjustment of the hybridization conditions to increase or decrease stringency (i.e., adjustment of hybridization pH, temperature or salt content of the buffer). Such minor modifications of the disclosed sequences and any necessary adjustments of hybridization conditions to maintain the 369 base pair DNA-specificity require only routine experimentation and are within the ordinary skill in the art. For example, for diagnostics applications, depending on the complexity of the target sequence, the oligonucleotide primer typically contains 15–25 or more nucleotides, although it may contain fewer nucleotides. For other applications, the oligonucleotide primer is typically shorter, e.g., 7–15 nucleotides.

The primers IS1SS and IS1SR3 of the primer composition of the present invention can be used in various ratios in detection of the *S. sonnei*. Ratios selected will depend upon several factors, including the method of detection used, the amount of nucleic acid material and the source of the biological sample. Preferably, the ratio of IS1SS to IS1SR3 is 1:1.

Primers are readily synthesized by standard techniques. Detailed procedures for the phospho-triester and hydrogen phosphonate methods of oligonucleotide synthesis are described in the U.S. Pat. No. 4,458,066.

Another object of the invention is to provide a method for detecting *Shigella sonnei* in a solution sample, which comprises the following steps:

(a) incubating said sample with primers IS1SS and IS1SR3 in a PCR reaction solution whereby a PCR reaction takes place which amplifies nucleic acids to produce a 369 base pair amplification product;

(b) detecting the presence of a 369 base pair amplification product;

(c) splicing the 369 base pair amplification product by restriction enzyme BstEII;

(d) detecting the presence of the DNA fragments of the 88 base pair and 281 base pair; wherein the presence of said DNA fragments are indicative of the presence of *Shigella sonnie* in the sample.

According to the invention, any suitable solution sample can be applied in the method of the invention. In particular, water sample containing less amount bacteria also can be applied in the method of the invention.

According to the invention, the method, before the above-mentioned step (a), further comprises a step of filtering the solution sample with a membrane and treating the membrane at a temperature for a time period, that is sufficient to lyse the bacteria in said solution. Preferably, the temperature in the method ranges from 85° C. to 97° C. and said time period ranges from 1 to 15 minutes.

According to the invention, any amplification protocol that utilizes cyclic, specific hybridization of primers to the target sequence, extension of the primers using the target sequence as a template and separation or displacement of the extension products from the target sequence may employ in the PCR reaction of the method of the invention. For amplification methods that do not require specialized, non-target binding sequences, the amplification primers may consist only of the target binding sequences of the amplification primers of the invention. As thermocycling is a feature of amplification by PCR, the restriction endonuclease is preferably added at low temperature after the final cycle of primer annealing and extension for end-point detection of amplification. Once amplified, the products can be analyzed by many techniques known in the art. For example, one technique uses physical separation of the amplification products to distinguish the products, such as electrophoresis, chromatograph and filtration. The preferred physical separation is electrophoresis.

According to the invention, the primers IS1SS and IS1SR3 amplify nucleic acids to produce a 369 base pair amplification product. Then, a restriction enzyme BstEII is used to splice the resulting 369 base pair amplification product. The presence of *Shigella sonnie* in the sample can be ensured when the DNA fragments of 88 base pair and 281 base pair are produced after splicing.

According the invention, the method of the invention has 100% specific detection for the *Shigella sonnie*.

While the invention is described above in relation to certain specific embodiments, it will be understood that many variations are possible, and that alternative materials and reagents can be used without departing from the invention. In some cases such variations and substitutions may require some experimentation, but will only involve routine testing.

EXAMPLES

Example 1

Figure 1:
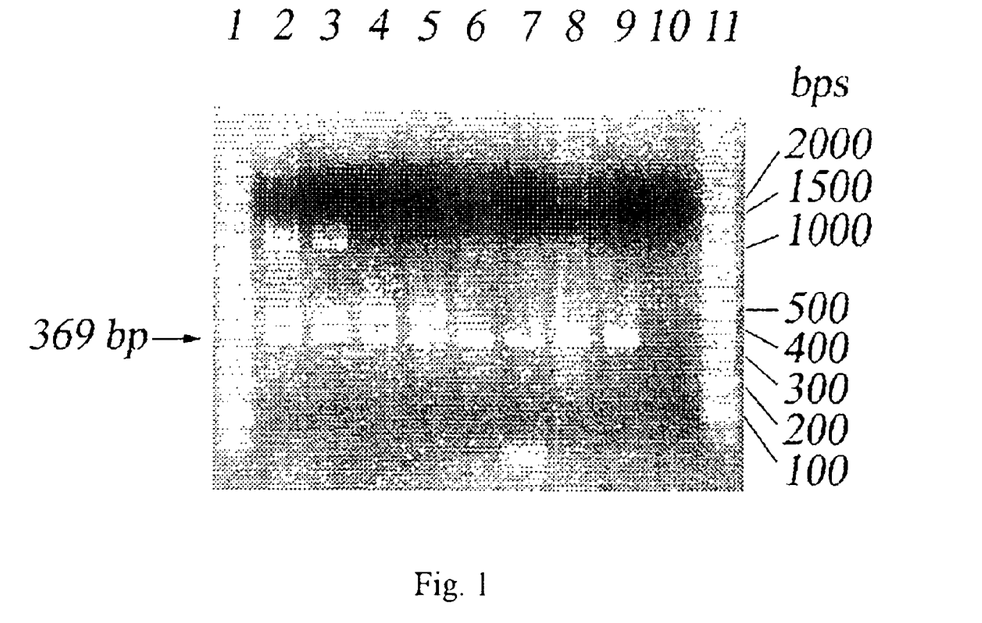
FIG. 1 shows the electrophoresis plot of the samples of the *S. boydii*, *S. dysenteriae*, *S. flexneri* and *S. sonnei*; Lane 1: 100 bp marker; Lane 2: *S. sonnei* diluted by $10^2$ times; Lane 3: *S. sonnei* diluted by $10^3$ times; Lane 4: *S. dysenteriae* diluted by $10^2$ times; Lane 5: *S. dysenteriae* diluted by $10^3$ times; Lane 6: *S. flexneri* diluted by $10^2$ times; Lane 7: *S. flexneri* diluted by $10^3$ times; Lane 8: *S. boydii* diluted by $10^2$ times; Lane 9: *S. boydii* diluted by $10^3$ times; Lane 10: sterile water; Lane 11: 100 bp marker.

*S. boydii* (ATCC 8700), *S. dysenteriae* (ATCC 4837), *S. flexneri* (ATCC 29903) and *S. sonnei* (ATCC 29930) were incubated in LB broth at 37° C. overnight. The resulting solution was diluted by $10^2$ and $10^3$ times with sterile water. 1 ml of the diluted solution was added to 50 ml water and then filtered by fluropore membrane. A PCR reaction was performed using IS1SS and IS1SR3 as primers and the resulting membrane as template. The PCR products were analyzed by gel electrophoresis. The resulting gel was dyed by ethidium bromide and observed under UV light. A control was prepared by adding 1 ml of sterile water to 50 ml water and conducted the PCR reaction as described above. As shown in FIG. 1, the samples of the *S. boydii, S. dysenteriae, S. flexneri* and *S. sonnei* diluted by $10^2$ and $10^3$ times have a band of 369 base pair DNA fragment in the gel (lanes 2–9) and the control does not have the band (lane 10).

Example 2

Figure 2:
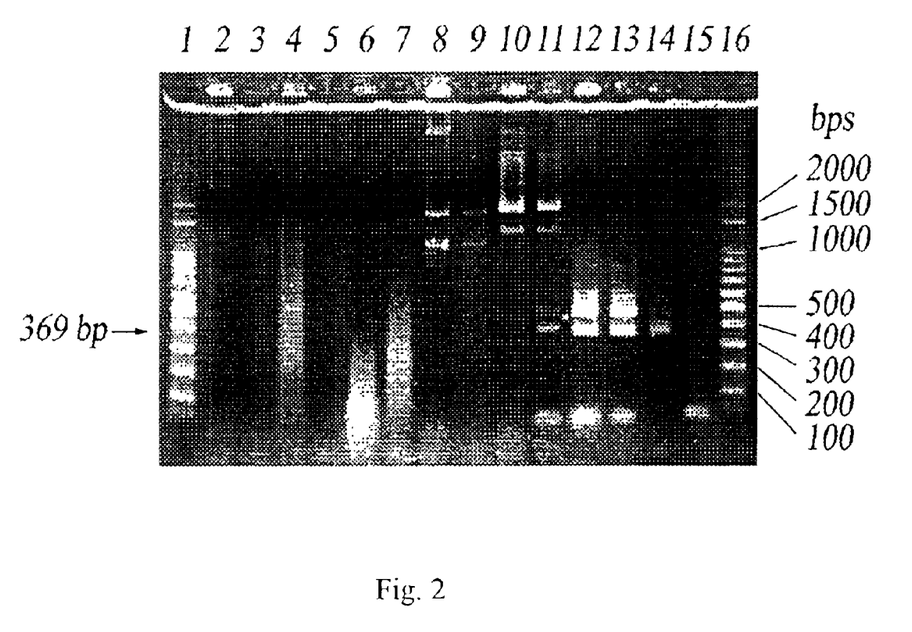

Escherichia W3110 (ATCC 27325), *Sallmonella choleraesuis* (ATCC 13311), *Klebsiella pneumoniae* (ATCC 13883) were incubated in LB broth at 37° C. overnight. *Serratia marcescens* (ATCC 13880) was incubated in LB broth at 25° C. overnight and *Enterobacter aerogenes* (ATCC 13048) and *Enterobacter cloacae* (ATCC 13047) were incubated in LB broth at 30° C. overnight. The resulting solutions were diluted by $10^2$ and $10^3$ times. 1 ml of the diluted solution was added to 50 ml water and then filtered by fluropore membrane. A PCR reaction was performed using IS1SS and IS1SR3 as primers and the resulting membrane as template. The PCR products were analyzed by gel electrophoresis. The resulting gel was dyed by ethidium bromide and observed under UV light. A control was prepared by adding 1 ml of sterile water to 50 ml water and conducted the PCR reaction as described above. As shown in FIG. 2, the sample of the *E. aerogenes* diluted by $10^3$ times or the sample of *E. coli* W3110 diluted by $10^2$ and $10^3$ times have a band of 369 base pair DNA fragment in the gel (lanes 11–13) and the sample of the *E. aerogenes* diluted by 10² times, the samples of *Sallmonella choleraesuis* (ATCC 13311), *Klebsiella pneumoniae* (ATCC 13883), *Serratia marcescens* (ATCC 13880) and *Enterobacter cloacae* (ATCC 13047) and the control does not have the band (lanes 2–10 and lane 15).

Example 3

Figure 3:
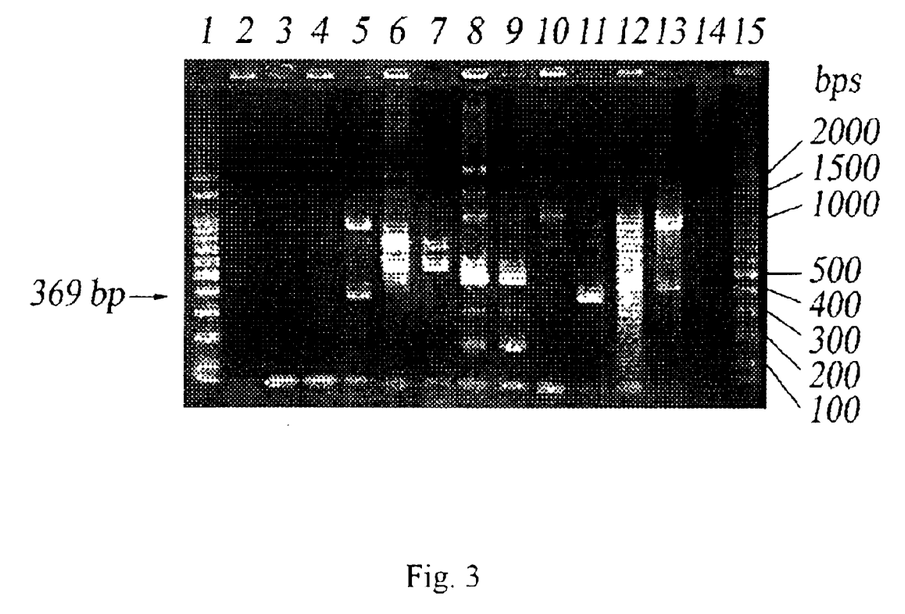
FIG. 3 shows the electrophoresis plot of the samples obtained from well water and incubated at 25° C.; Lane 1: 100 bp marker; Lane 2: *P. syclowiorum* diluted by $10^2$ times; Lane 3: *P. syclowiorum* diluted by $10^3$ times; Lane 4: *S. odorifera* diluted by $10^2$ times; Lane 5: *S. odorifera* diluted by $10^2$ times; Lane 6: *P. agglomerans* diluted by $10^2$ times; lane 7: *P. agglomerans* diluted by $10^3$ times; Lane 8: *E. hermanii* diluted by $10^2$ times; Lane 9: *E. hermanii* diluted by $10^3$ times; Lane 10: *A. calcoacet/baumannii*/gen 2 diluted by $10^2$ times; Lane 11: *A. calcoacet/baumannii*/gen 2 diluted by $10^3$ times; Lane 12: *S. marcescens* diluted by $10^2$ times; Lane 13: *S. marcescens* diluted by $10^3$ times; Lane 14: sterile water; Lane 15: 100 bp marker.
Figure 4:
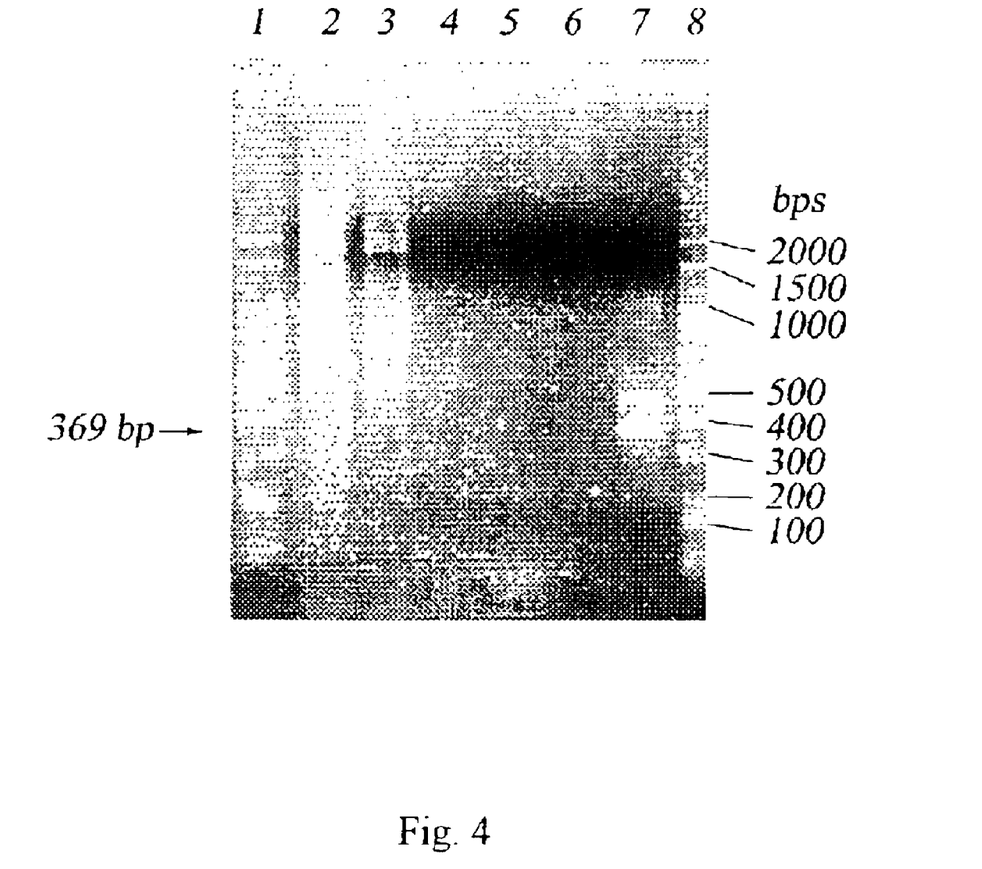
FIG. 4 shows the electrophoresis plot of the samples obtained from well water and incubated at 20° C.; Lane 1: 100 bp marker; Lane 2: *A. johnsonii* diluted by $10^2$ times; Lane 3: *A. johnsonii* diluted by $10^3$ times; Lane 4: *S. capitis* diluted by $10^2$ times; Lane 5: *S. capitis* diluted by 10 times; Lane 6: water; Lane 7: *S. sonnei*; Lane 8: 100 bp marker.
Figure 5:
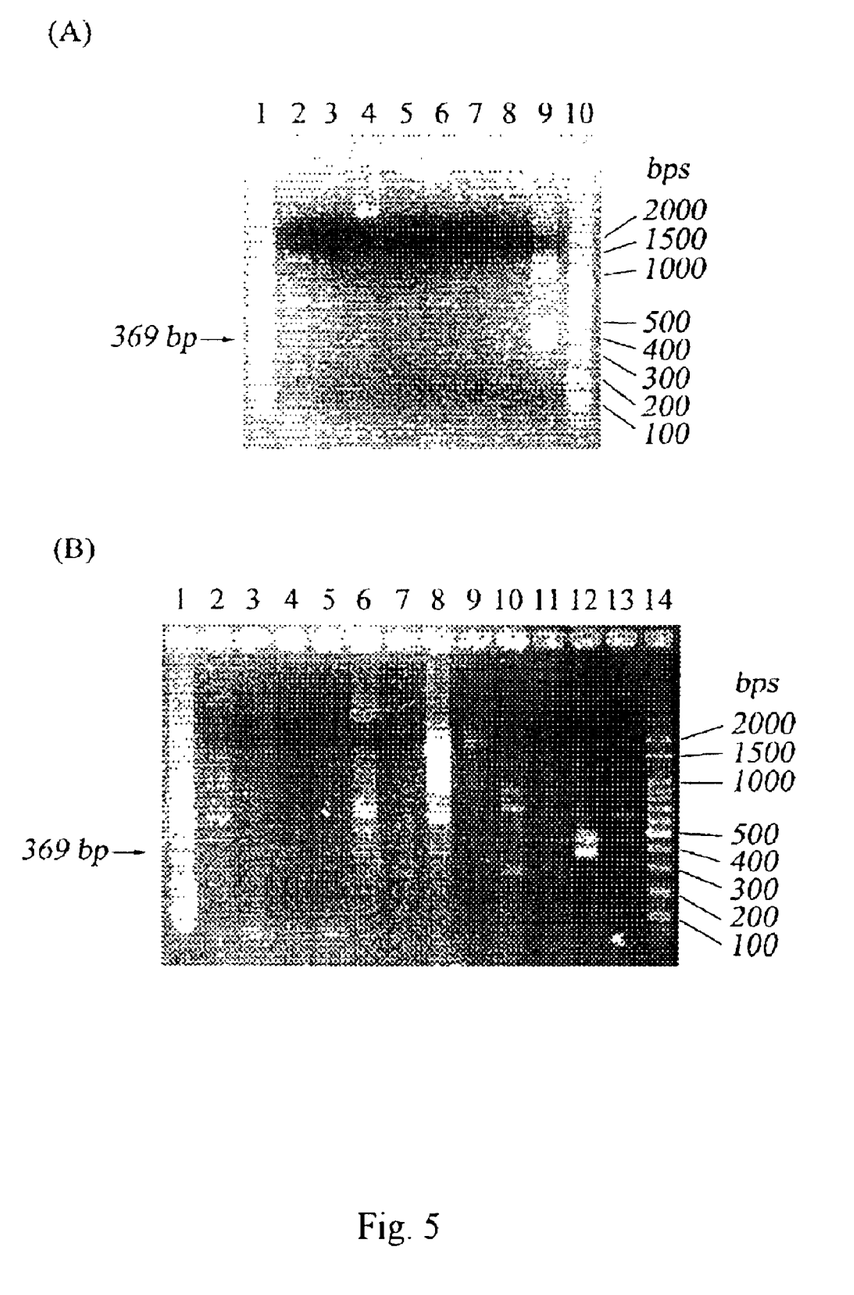

The ground water sample and well water sample were incubated in LB broth at 20° C. or 25° C. 16 strains were isolated from the samples and then identified. One strain cannot be identified and two strains were dead during the identification. Six strains, *P. syclowiorum, S. odorifera, P. agglomerans, E. hermanii, A. calcoacet/baumannii*/gen 2 and *S. marcescens*, were identified from the well water incubated at 25° C. Two strains, *A. johnsonii* and *S. capitis*, were identified from the well water incubated at 20° C. Five strains, *O. ureolytica/urethralis, X. maltophilia, A. delafieldii, X. maltophilia* and *A. genospecies* 15, were identified from the ground water incubated at 25° C. The 16 strains were incubated in LB broth overnight. The resulting solutions were diluted with sterile water. The resulting solutions were diluted by $10^2$ and $10^3$ times. 1 ml of the diluted solution was added to 50 ml water and then filtered by fluropore membrane. A PCR reaction was performed using IS1SS and IS1SR3 as primers and the resulting membrane as template. The PCR products were analyzed by gel electrophoresis. The resulting gel was dyed by ethidium bromide and observed under UV light. A control was prepared by adding 1 ml of sterile water to 50 ml water and conducted the PCR reaction as described above. As shown in FIGS. 3, 4 and 5, the sample of the *S. odorifera* or *A. calcoacet/baumannii*/gen diluted by $10^3$ times and the sample of *S. marcescens* diluted by $10^2$ and $10^3$ times have a band of 369 base pair DNA fragment in the gel (lanes 5 and 11–13). The other samples and the control do not have the band.

Example 4

Figure 6:
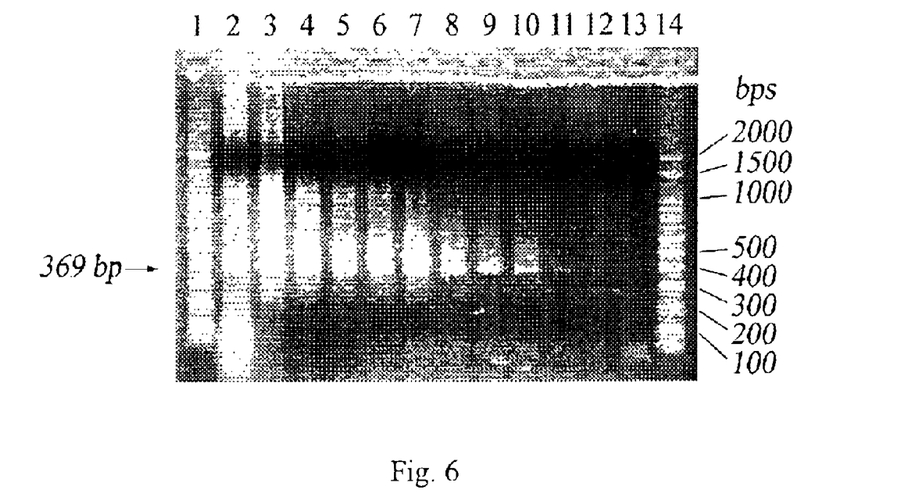
FIG. 6 shows the electrophoresis plot of *S. sonnei* (ATCC 29930) diluted by serial 10 times; Lane 1: 100 bp marker; Lane 2: dilution by 10 times; Lane 3: dilution by $10^2$ times; Lane 4: dilution by $10^3$ times; Lane 5: by $10^4$ times; Lane 6: dilution by $10^5$ times; Lane 7: dilution by $10^6$ times; Lane 8: dilution by $10^7$ times; Lane 9: dilution by $10^8$ times; Lane 10: dilution by $10^9$ times; Lane 11: dilution by $10^{10}$ times; Lane 12: dilution by $10^{11}$ times; Lane 13: sterile water; Lane 14: 100 bp marker.

*S. sonnei* (ATCC 29930) was incubated in LB broth at 37° C. overnight to $3.4×10^{10}$ CFU/ml. The resulting solution was serially diluted by 10 to $10^{11}$ times. 1 ml of the diluted solution was added to 50 ml water and then filtered by fluropore membrane. A PCR reaction was performed using IS1SS and IS1SR3 as primers and the resulting membrane as template. The PCR products were analyzed by gel electrophoresis. The resulting gel was dyed by ethidium bromide and observed under UV light. A control was prepared by adding 1 ml of sterile water to 50 ml water and conducted the PCR reaction as described above. As shown in FIG. 6, the samples of the *S. sonnei* diluted by 10 to $10^{10}$ times have a band of 369 base pair DNA fragment in the gel (lanes 2–11) and the sample of the *S. sonnei* diluted by $10^{13}$ times and the control do not have the band (lanes 2 and 13). Therefore, the *S. sonnei* could be detected as loon as the sample contained more than 3.4 cells. That is, the sensitivity of the method of the invention can reach 3.4 cells per sample.

Example 5

The 369 bp PCR products of *S. boydii* (ATCC 8700), *S. dysenteriae* (ATCC 4837), *S. flexneri* (ATCC 29903), *S. sonnei* (ATCC 29930), *E. coli* W3110 (ATCC 27325), *E. aerogenes* (ATCC 13048), *S. odorifera, P. agglomerans* and *S. marcescens* obtained in Examples 1 to 3 were sliced by restriction enzyme BstEII and then analyzed by gel electrophoresis.

Figure 7:
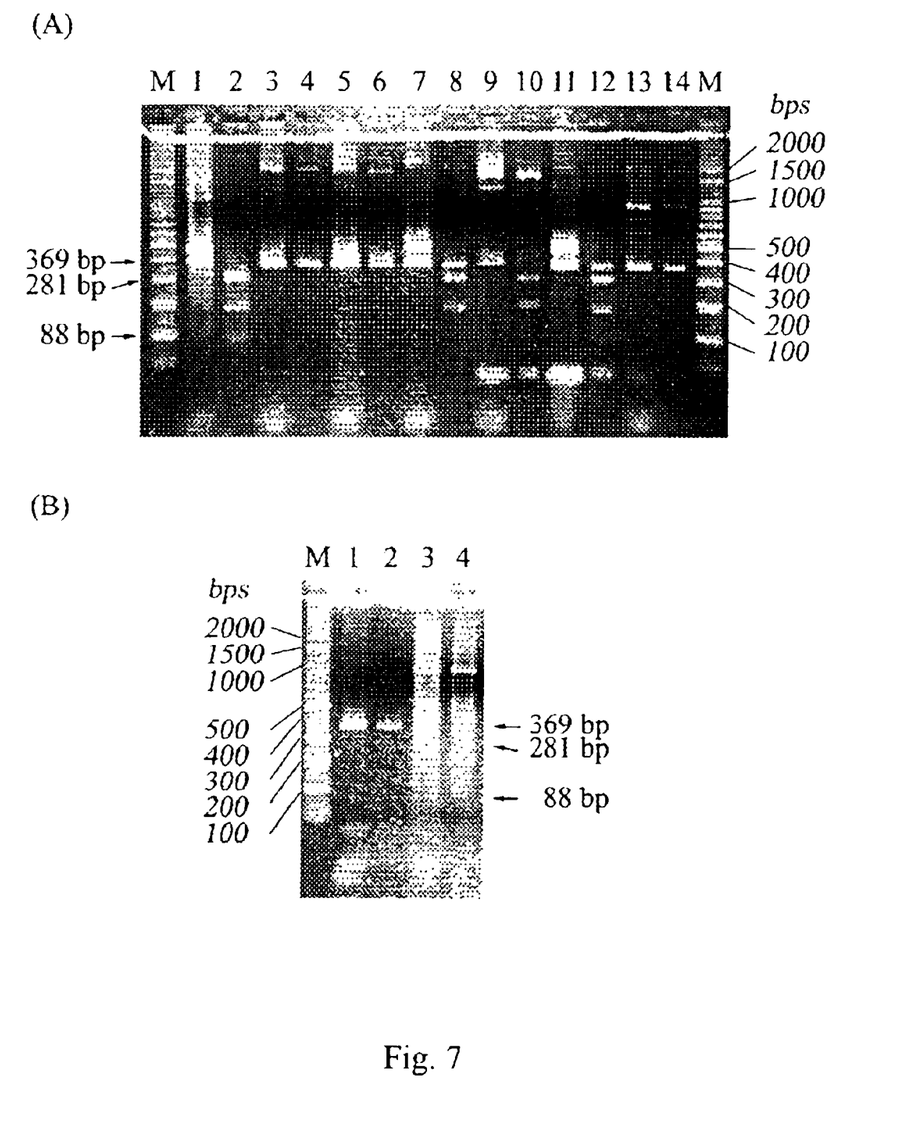

The resulting gel was dyed by ethidium bromide and observed under UV light. As shown in FIG. 7, only the 369 bp PCR product of *S. sonnei* (ATCC 29930) was sliced to 88 bp and 281 bp DNA fragments. The other strains did not produce the 88 bp and 281 bp DNA fragments.

Example 6

Figure 8:
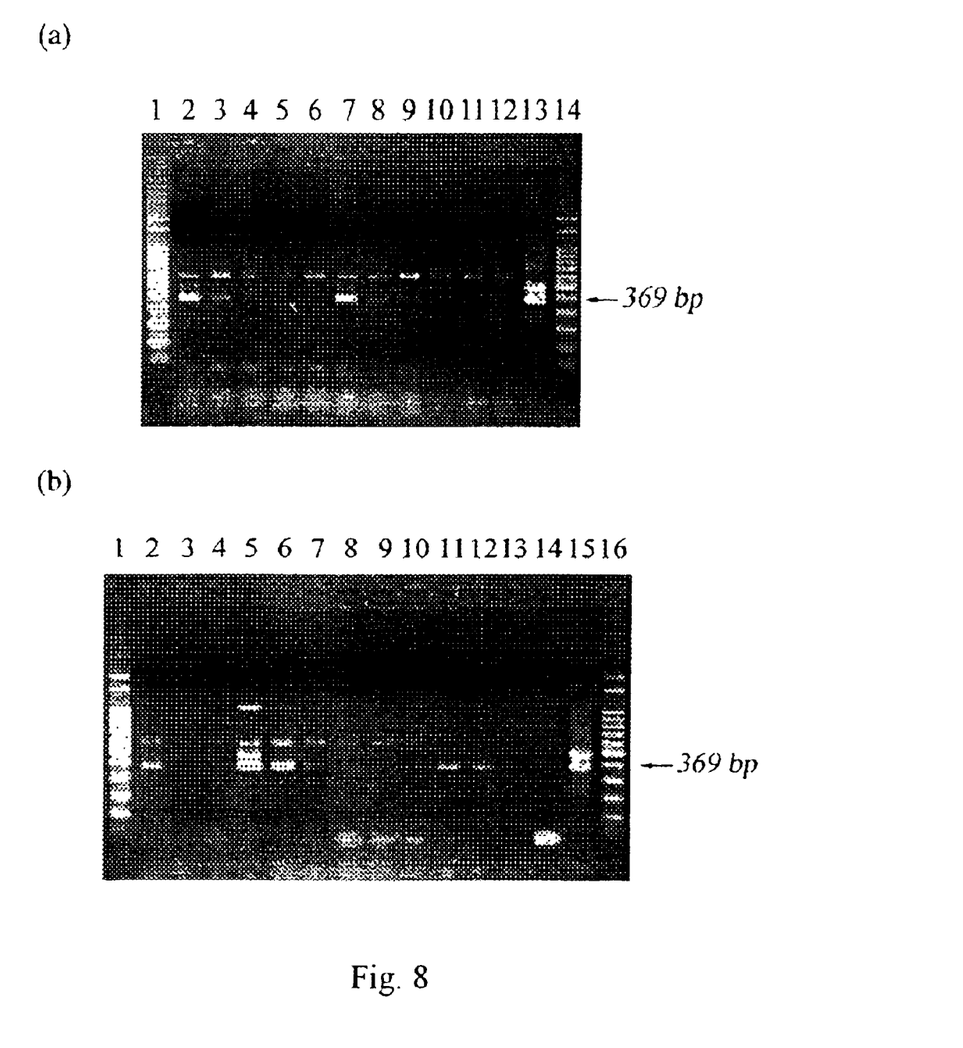
Figure 9:
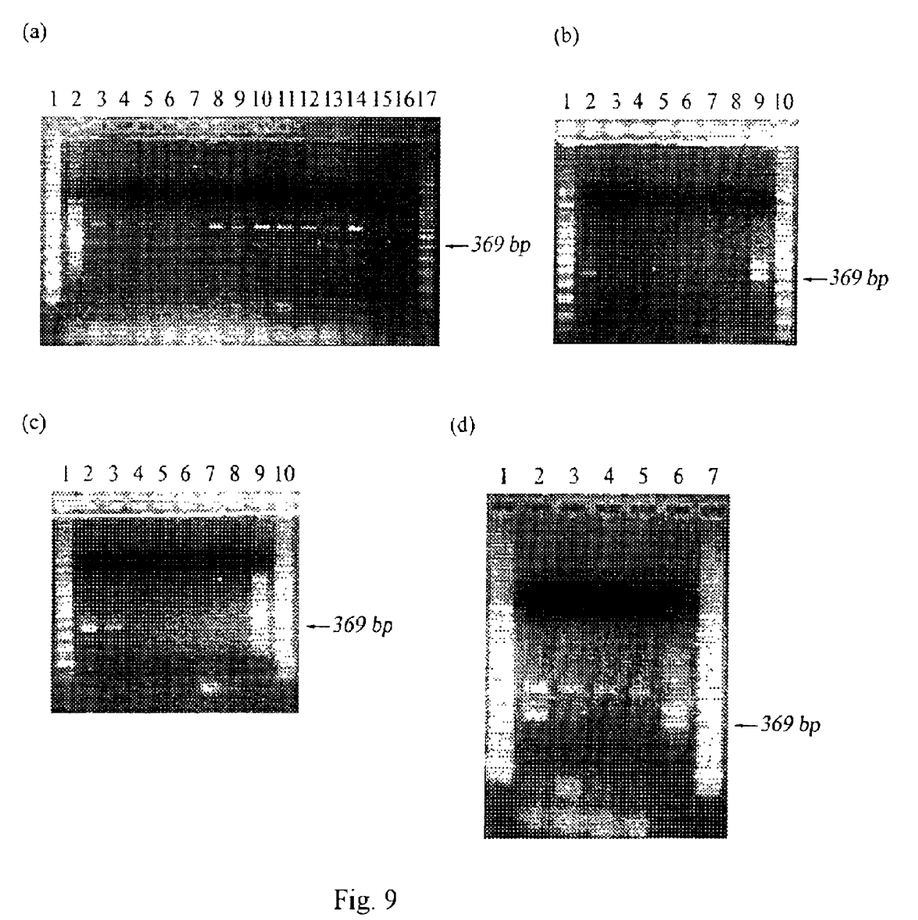
Figure 10:
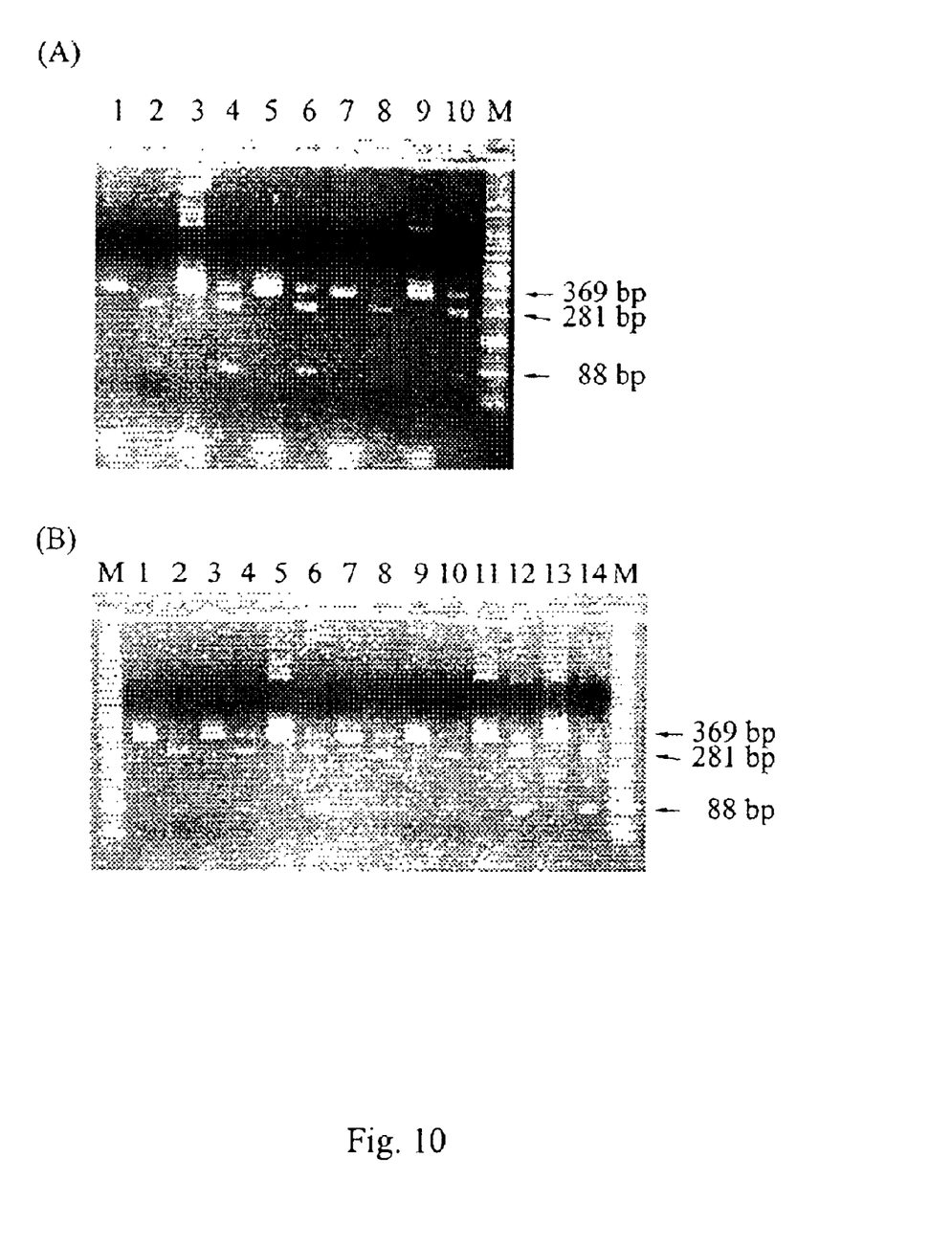
FIG. 10 shows the electrophoresis plot of the BstEII sliced fragments of the 369 bp products of *S. sonnei*, the lanes of odd numbers represent the PCR products that were not cut by the BstEII and the lanes of even numbers represent the PCR products that were cut by the BstEII; (A) Lane M: 100 bp marker; Lanes 1 and 2: *S. sonnei* (ATCC 11060); Lanes 3 and 4: *S. sonnei* (ATCC 25931); Lanes 5 and 6: *S. sonnei* (ATCC 20920); Lanes 7 and 8: *S. sonnei* (ATCC 29031); Lanes 9 and 10: *S. sonnei* (south 27); (B) Lane M: 100 bp marker; Lanes 1 and 2: *S. sonnei* (south 36); Lanes 3 and 4: *S. sonnei* (SH 10567); Lanes 5 and 6: *S. sonnei* (SH 7105); Lanes 7 and 8: *S. sonnei* (SH 8255); Lanes 9 and 10: *S. sonnei* (SH 9397); Lanes 11 and 12: *S. sonnei* (SH 8069); Lanes 13 and 14: *S. sonnei* (ATCC 9290).

Five *S. sonnei* strains obtained from ATCC (American Type Culture Collection, Maryland, U.S.A), ATCC 9290, ATCC 11060, ATCC 25931, ATCC 20920 and ATCC 29031 and seven *S. sonnei* isolated from Taiwan, SH7105, SH8069, SH8255, SH10567, South 27 and South 26, were incubated in LB broth at 37° C. overnight and then diluted by serial 10 times. 1 ml of the diluted solution was added to 50 ml water and then filtered by fluropore membrane. A PCR reaction was performed using IS1SS and IS1SR3 as primers and the resulting membrane as template. The PCR products were analyzed by gel electrophoresis. The resulting gel was dyed by ethidium bromide and observed under UV light. A control was prepared by adding 1 ml of sterile water to 50 ml water and conducted the PCR reaction as described above. As shown in FIGS. 8 and 9, the samples of the twelve *S. sonnei* strains have a band of 369 base pair DNA fragment in the gel and the control does not have the band. The 369 bp PCR products were sliced by restriction enzyme BstEII and then analyzed by gel electrophoresis. As shown in FIG. 10, the twelve strains have 88 bp and 281 bp DNA fragments.

What is claimed is:

1. A PCR primer composition that specifically amplifies a 369 base pair DNA of *Shigella sonnei*, said composition comprising the primers IS1SS and IS1SR3 wherein the primer IS1SS comprises the sequence as defined in SEQ ID NO:1 and the primer IS1SR3 comprises the sequence as defined in SEQ ID NO:2.

2. A method for detecting *Shigella sonnei* in a solution sample, which comprises the following steps:

(a) incubating said sample with primers IS1SS and IS1SR3 as claimed in claim 1 in a PCR reaction solution whereby a PCR reaction takes place which amplifies nucleic acids to produce a 369 base pair amplification product;

(b) detecting the presence of a 369 base pair amplification product;

(c) splicing the 369 base pair amplification product by restriction enzyme BstEII;

(d) detecting the presence of the DNA fragments of the 88 base pair and 281 base pair; wherein the presence of said DNA fragments are indicative of the presence of *Shigella sonnie* in the sample.

3. The method according to claim 2, which, before the step (a), further comprises a step of filtering the solution sample with a membrane and treating the membrane at a temperature for a time period, that is sufficient to lyse the bacteria in said solution.

4. The method according to claim 3, wherein said temperature ranges from 85° C. to 97° C. and said time period ranges from 1 to 15 minutes.

5. The method according to claim 2, wherein the PCR product and the DNA fragments are detected by gel electrophoresis.

* * * * *